(12) United States Patent
Hagar et al.

(10) Patent No.: US 10,323,157 B2
(45) Date of Patent: Jun. 18, 2019

(54) SILVER-SILVER CHLORIDE COMPOSITIONS AND ELECTRICAL DEVICES CONTAINING THE SAME

(71) Applicant: Parker-Hannifin Corporation, Cleveland, OH (US)

(72) Inventors: Jesse A. Hagar, Woburn, MA (US); Nicholas Pascucci, Woburn, MA (US)

(73) Assignee: Parker-Hannifin Corporation, Cleveland, OH (US)

( * ) Notice: Subject to any disclaimer, the term of this patent is extended or adjusted under 35 U.S.C. 154(b) by 0 days.

(21) Appl. No.: 15/748,359

(22) PCT Filed: Aug. 22, 2016

(86) PCT No.: PCT/US2016/047999
§ 371 (c)(1),
(2) Date: Jan. 29, 2018

(87) PCT Pub. No.: WO2017/031487
PCT Pub. Date: Feb. 23, 2017

(65) Prior Publication Data
US 2018/0215941 A1    Aug. 2, 2018

Related U.S. Application Data

(60) Provisional application No. 62/207,684, filed on Aug. 20, 2015.

(51) Int. Cl.
*H01B 1/22* (2006.01)
*C09D 5/00* (2006.01)
(Continued)

(52) U.S. Cl.
CPC ............... *C09D 11/52* (2013.01); *C09D 5/12* (2013.01); *C09D 11/03* (2013.01); *C09D 11/037* (2013.01);
(Continued)

(58) Field of Classification Search
CPC .... H01B 1/00; H01B 1/22; C09D 5/24; A61B 5/0408
See application file for complete search history.

(56) References Cited

U.S. PATENT DOCUMENTS 3,834,373 A     9/1974  Sato
4,450,188 A *   5/1984  Kawasumi ............. B22F 1/025
                                                    252/513
(Continued)

FOREIGN PATENT DOCUMENTS

WO     WO 2005/116702    * 12/2005

OTHER PUBLICATIONS

The International Search Report and the Written Opinion of the International Search Authority for corresponding International Application No. PCT/US2016/047999 dated Nov. 9, 2016.
(Continued)

*Primary Examiner* — Mark Kopec
(74) *Attorney, Agent, or Firm* — Renner, Otto, Boisselle & Sklar, LLP

(57) ABSTRACT

The present disclosure provides plated particles for use in silver/silver chloride ink for making medical devices. The plated particles include a plurality of silver coated inert particles. The silver coating of each silver coated inert particle is about 10 to 50% by weight of the silver coated inert particle. The silver/silver chloride ink includes a plurality of silver coated inert particles and a plurality of silver chloride particles. A medical device includes a backing layer, a silver/silver chloride ink layer and a conductive adhesive layer.

20 Claims, 3 Drawing Sheets

(51) Int. Cl.
    *C09D 11/00*     (2014.01)
    *C09D 11/52*     (2014.01)
    *C09D 5/12*      (2006.01)
    *C09D 11/03*     (2014.01)
    *C09D 11/037*    (2014.01)
    *A61B 5/0408*    (2006.01)
    *C01G 5/02*      (2006.01)
(52) U.S. Cl.
    CPC .............. *H01B 1/22* (2013.01); *A61B 5/0408* (2013.01); *C01G 5/02* (2013.01)

(56)         References Cited

U.S. PATENT DOCUMENTS 4,877,512  A      10/1989  Bowns et al.
    5,051,208  A       9/1991  Bowns et al.
    5,207,950  A       5/1993  Ehrreich
    5,565,143  A      10/1996  Chan
    5,851,438  A  *   12/1998  Chan ................... A61N 1/0436
                                                            252/514
    5,855,820  A       1/1999  Chan
    9,255,208  B2 *    2/2016  Dorfman ................ C09D 11/52

OTHER PUBLICATIONS

The International Preliminary Report on Patentability for corresponding International Application No. PCT/US2016/047999 dated Nov. 10, 2017.

* cited by examiner

SILVER-SILVER CHLORIDE COMPOSITIONS AND ELECTRICAL DEVICES CONTAINING THE SAME

This application is a national phase of International Application No. PCT/US2016/047999filed on Aug 22, 2016 and published in the English language, and claims priority to U.S. Provisional Application No. 62/207,684 filed on Aug. 20, 2015, which are incorporated herein by reference.

TECHNICAL FIELD

The present disclosure relates generally to conductive compositions, and more particularly to silver-silver chloride compositions containing silver coated inert particles for use in making electrochemical and biomedical electrodes.

BACKGROUND

Medical devices are used in a number of applications for a variety of diagnostic and monitoring purposes. For instance, electrodes are commonly used to monitor physiological electric potentials to detect muscular activity of a person's heart. The cardiovascular activity of the heart is typically monitored by adhering or connecting electrodes to the skin of the patient at particular locations on the body. The electrodes are then electrically coupled to electrical equipment such as an electrocardiograph (also referred to as ECG or EKG) apparatus that monitors the muscular activity of the heart. The resulting traces or output of the ECG provide a diagnostic tool for detecting heart disease and/or heart dysfunction of various etiology.

Silver-silver chloride inks are conventionally used in electrochemical and biomedical electrodes. Conductive Ag/AgCl ink is printed on polymeric film substrates to provide relatively low cost, disposable electrodes for ECG and other medical electrode applications.

SUMMARY

The present disclosure relates to conductive compositions that include silver coated inert particles, silver chloride particles and at least one polymeric binder. The conductive compositions are useful as conductive inks, and in particular, for printing on substrates to make disposable electrodes for use in biomedical applications.

In accordance with one aspect of the present disclosure, there is provided a conductive composition that includes, based on dry weight, 5-30% silver coated inert particles having a particle size in the range of 1 μm to 100 μm and having a silver content of 55 wt % or less, based on the weight of the coated inert particles; 5-30% AgCl; and 5-30% polymeric binder; wherein the surface area ratio of Ag/AgCl is in the range of 1:2 to 8:1.

The inert particles may be made of glass, and in one embodiment, glass flakes.

The conductive composition may further include 0.5-25 wt % Ag particles. In one embodiment, the Ag particles are Ag flakes and the Ag flake content is within the range of 5-20% by weight. The Ag flake particles have an average particle size of 5 microns to 45 microns.

The AgCl of the conductive composition may have an average particle size in the range of 0.1 micron to 15 microns.

The Ag-coated inert particles, AgCl particles, Ag particles if present, and binder may be dispersed in 10-90 wt % organic solvent.

In one embodiment, the silver coated inert particles are made up of 10-45 wt % silver and 55-90 wt % inert particle.

In one embodiment, the average particle size of the silver coated inert particles is within the range of 1 to 20 μm and the coated particles comprise 35-45 wt % silver and 55-65 wt % inert particle. In another embodiment, the average particle size of the silver coated inert particles is within the range of 10 to 100 μm and the coated particles comprise 10-35 wt % silver and 65-90 wt % inert particle.

In another aspect, there is provided a biomedical electrode that includes: a conductor including an electrically conductive surface; a conductive ink layer in electrical contact with the conductor, the ink layer being the Ag/AgCl conductive composition described herein; and an electrically conductive adhesive in electrical contact with the conductive ink layer.

The electrically conductive surface of the biomedical electrode may include a graphite loaded polymer. The graphite loaded polymer may be in the form of a graphite containing ink layer, or a graphite containing polymeric film, such as a graphite vinyl film.

The biomedical electrode may further include a non-conductive backing layer having a first side including a first major surface and a second side including a second major surface, the electrically conductive surface associated with the second major surface of the non-conductive backing and the electrically conductive adhesive associated with the electrically conductive surface.

In one embodiment, the electrically conductive adhesive may be a pressure sensitive adhesive. In another embodiment, the electrically conductive adhesive includes a hydrogel.

The non-conductive backing of the biomedical electrode may further include a tab portion and a conductive interface portion, the first major surface and the second major surface shared by the tab portion and the conductive interface portion, at least a portion of the electrically conductive adhesive being disposed over the second major surface on the conductive interface portion, the electrically conductive adhesive associated with the electrically conductive surface on the conductive interface portion.

The biomedical electrode may further include a release liner disposed over the electrically conductive adhesive.

In the description that follows, to illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

DETAILED DESCRIPTION

The present invention relates to conductive compositions that include silver coated inert particles and silver chloride particles. The conductive compositions may be used in medical devices such as biomedical electrodes.

The conductive composition generally includes silver coated inert particles, silver chloride particles, and a binder into which the silver coated particles and silver chloride particles are dispersed. The conductive composition may be used as a conductive coating or ink layer.

Figure 1:
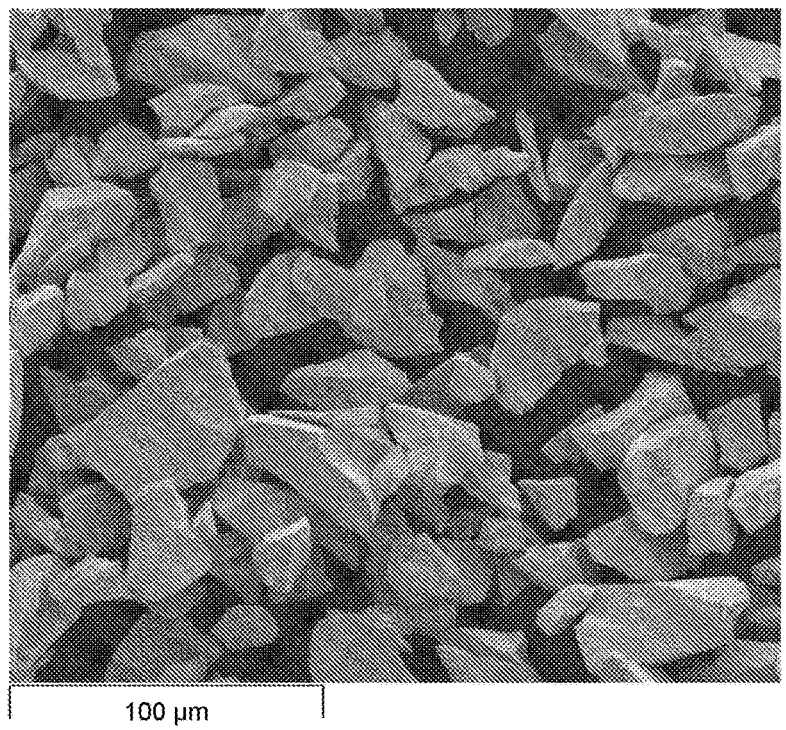
FIG. 1 is an SEM image showing Ag coated glass particles according to an embodiment of the present invention.

Referring initially to FIG. 1, exemplary silver coated particles according to the present disclosure are shown. The plated particles shown in the SEM image include an inner glass flake and an outer silver coating covering the exterior surface of the glass flake.

Figure 2:
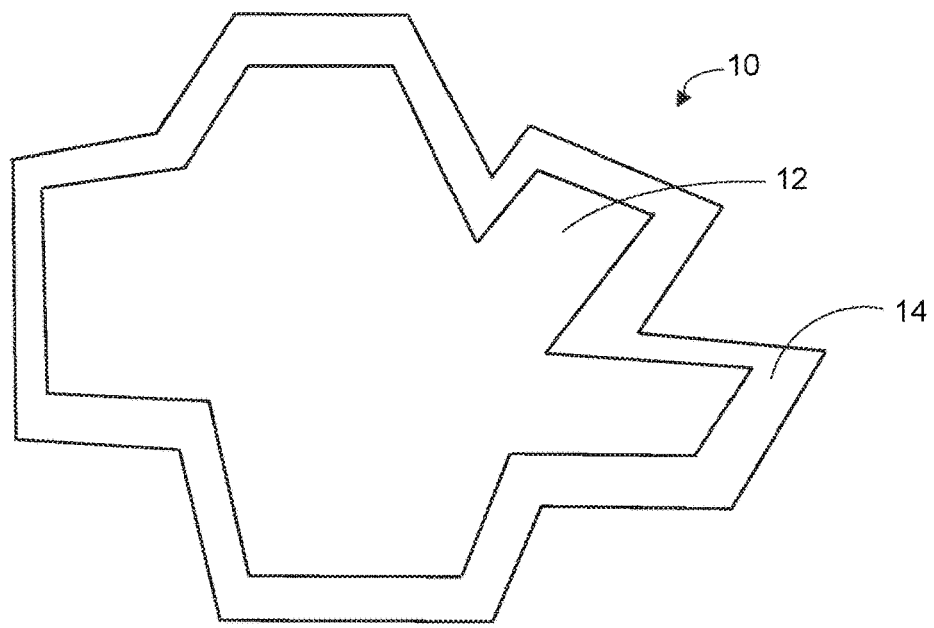
FIG. 2 is a cross-sectional view of an exemplary silver coated inert particle according to the present invention.

As illustrated in FIG. 2, the plated particle 10 includes an inert particle 12 having a silver coating 14 on the exterior surface of the inert particle 12. The silver coated particles 10 are irregularly shaped, having a multitude of facets and jogs in the exterior surface, which increases the effective surface area of the particle as compared to round or platelet-like particles. The greater surface area allows more silver to be deposited on the individual inert particles. In a preferred embodiment, the inert particles are glass flakes.

When referring to flake size measurement, the length of the largest dimension of the flake is measured. The silver plated particle 10 may have a size in the range of about 0.5 to 100 microns, or in another example, in the range of about 5 microns to 75 microns, or in another example, in the range of about 5 microns to 50 microns.

In one embodiment, the particle size distribution D50 (also known as the median diameter or the medium value of the particle size distribution) of the Ag coated inert particles is within the range of 8 µm to 40 µm. In one embodiment, the specific surface area of the Ag coated inert particles is within the range of 0.3 to 1.2 $m^2/g$.

As used herein, "inert" refers to materials that will not interfere with the electric potential between the silver and the silver chloride, and will not react with the silver chloride. The inert particle 12 may preferably be made of glass. The inert particle 12 may be made of mica, plastic, ceramic or a combination thereof.

The silver coating 14 may be in the range of about 10% to 55% by weight of the silver coated inert particle, or in another example, in the range of about 15% to 50% by weight of the silver coated inert particle, or in another example, in the range of about 15% to 49% by weight of the silver coated inert particle, or in another example, in the range of 20% to 45% by weight of the silver coated inert particle. In one preferred embodiment, the silver coating is less than 50% by weight of the silver coated inert particle.

In one embodiment, the average particle size of the silver coated inert particles is within the range of 1 to 20 µm and the coated particles comprise 35-45 wt % silver and 55-65 wt % inert particle. In another embodiment, the average particle size of the silver coated inert particles is within the range of 10 to 100 µm and the coated particles comprise 10-35 wt % silver and 65-90 wt % inert particle.

Prior to the application of the silver coating 14, the inert particle 12 may be washed in a solution containing monosodium phosphate. The washed inert particle 12 may be etched with fluoroboric acid. The etched inert particle 12 may be activated with a solution containing hydrochloric acid and stannous chloride.

In one embodiment, the silver coating 14 may be applied to the inert particle 12 by an electroless plating technique. The electroless plating bath may be created with: (1) either ammonium hydroxide or potassium hydroxide to raise the pH; (2) tetraethylenepentamine (TEPA) as the chelating agent; (3) saccharine sodium as a grain refiner (i.e., brightener); and (4) silver nitrate as the silver source. Hydrazine is slowly introduced to the plating bath, which reduces the silver nitrate to elemental silver. As the hydrazine is pumped in, silver continually adheres to the surface of the inert particle. The hydrazine drip is maintained until all of the silver nitrate is reduced. After the final rinse, the silver-plated glass flake is dried in an oven at 160° F. for 7 hours. The flake is then ready for use in an ink composition.

Commercially available silver/silver chloride inks (e.g., ELECTRODAG PE-007, Henkel Corporation (Irvine, Calif.)) contain silver flakes and silver chloride powder. The silver flakes are generally pure silver, which leads to increased costs. Incorporating silver coated inert particles in the ink in place of some or all of the pure silver flakes reduces the cost of the ink, while maintaining the electrical performance of the ink layer.

The amount of silver chloride in the ink may be in the range of about 5 to 40% by weight of the dried ink, or in another example, 5 to 30% by weight of the dried ink, or in another example, 10 to 25% by weight of the dried ink, or in another example, 15 to 25% by weight of the dried ink.

The silver chloride particles may be in powder form or a wet paste. The average particle size of a silver chloride particles may be in the range of about 0.1 micron to 15 microns, or in another example, in the range of about 1 micron to 10 microns. A silver chloride powder, such as those commercially available from Colonial Metals Inc., DE or Metz Metallurgical Corporation, NJ, tends to agglomerate to form dry lumps which are difficult to disperse in liquid media by agitation. Therefore, milling and grinding in a suitable liquid medium may be needed to prepare fine dispersions of the silver chloride particles. Alternatively, a wet paste of fine silver chloride particles precipitated from an aqueous solution may be added directly to a water based silver ink mixture to make silver/silver chloride inks.

Alternatively, the silver chloride particles may be treated with a surfactant, such as the silver chloride particles commercially available from Metalor (North Attleborough, Mass.) to prevent the powder from agglomerating. Coating the silver chloride particles with a surfactant may be preferred when the inert particle of the silver coated particle is fragile, such as when the inert particle is glass.

A proper balance of silver to silver chloride is important to achieve the desired electrochemical characteristics of a silver/silver chloride medical electrode. Commercially available silver/silver chloride inks generally have a silver to silver chloride weight ratio of between 70:30 and 90:10.

In the conductive composition of the present invention, because the silver is provided as a coating on inert particles rather than as solid silver particles, the weight ratio of Ag/AgCl is generally lower than commercially available Ag/AgCl ink formulations. In one embodiment of the present invention, the silver to silver chloride weight ratio is about 49:30.

In some embodiments of the conductive composition, pure silver flakes may be added with the silver plated inert particles 10 to the conductive composition. "Pure silver" refers to a material that has a silver content of 99.9% by weight. The pure silver may be added to increase the overall silver content of the conductive composition. The amount of pure silver in the ink may be in the range of about 0.5-25% by weight of the dried ink, or in another example, 5 to 20% by weight of the dried ink, or in another example, 10 to 20% by weight of the dried ink. The average particle size of a silver flake particles may be in the range of about 5 microns to 45 microns, or in another example, in the range of about 10 microns to 40 microns. When referring to flake size measurement, the length of the largest dimension of the flake is generally measured.

The ink may further include a binder. The binder may include monomers that polymerize in situ, or may contain polymers. Suitable polymers are dependent on the type of medical device and the application of the medical device. Polymers may be selected from among polypyrrolidone, epoxies, phenolic resins, acrylics, urethanes, silicones and combinations of two or more thereof. Other polymers that may be included are styrene allyl alcohols, polyalkylene carbonates and/or polyvinyl acetals. The binder may be a single binder or two or more binders used in combination. In one embodiment, the binder includes a thermoplastic polyurethane.

The amount of binder in the ink may be in the range of about 5 to 30% by weight of the dried ink, or in another example, from about 5 to 25% by weight of the dried ink, or in another example, from about 10 to 25% by weight of the dried ink, or in another example, from about 15 to 25% by weight of the dried ink.

The ink may further include a solvent. One purpose of the solvent is to serve as a medium for dispersion of the binder and the particles (i.e., silver coated inert particles and silver chloride particles). Thus, the solvent should be a compatible solvent for the polymer so that a stable, uniform dispersion of inorganic fillers in the polymer solution may be formed. Secondly, the properties of the solvent should be such that they lend acceptable application properties to the composition. For example, a suitable solvent and binder system may be chosen based on the method by which the conductive ink is applied or printed on a particular substrate. Examples of application processes include screen printing, ink jet printing, flexographic/gravure printing, rotogravure printing, knife coating and the like.

The solvent may include alcohols, ethers, esters, ketone, water or a combination thereof. In one embodiment, the solvent is selected from among methyl ethyl ketone, propylene glycol monomethyl ether, propylene glycol monomethyl ether acetate, and combinations or two or more thereof. The amount of solvent in the ink may be in the range of about 10 to 90% by weight of the ink composition, or in another example, from about 15 to 60% by weight of the ink composition, or in another example, about 20 to 50% by weight of the ink composition.

The ratio of the silver coated inert particles and silver chloride particles (i.e., particles) to the solvent and binder (i.e., vehicle) may vary considerably and depends upon the method by which the ink is to be applied and the kind of solvent and binder used.

In one embodiment the ratio of the surface area of silver to the surface area of AgCl is within the range of 1:2 to 8:1. In another example, the ratio of the surface area of Ag/AgCl is within the range of 1:1.5 to 7:1, or in another example the ratio of the surface area of Ag/AgCl is within the range of 1:1.5 to 6:1.

The ink may be made by placing the silver coated inert particles, silver chloride particles, binder and solvent into a mixing vessel and mixing the materials until a homogenous mixture is obtained. In Table I below, relative amounts of the components of exemplary conductive Ag/AgCl ink are given.

TABLE I

| Dry Ink Content | Wt % |
| --- | --- |
| Ag Coated Inert Particle (Ag-glass) | 35-80% |
| Pure Ag Flake (R1045) | 0-25% |
| Silver Chloride (R1242) | 5-30% |
| Binder (TPU) | 5-30% |

Figure 3:
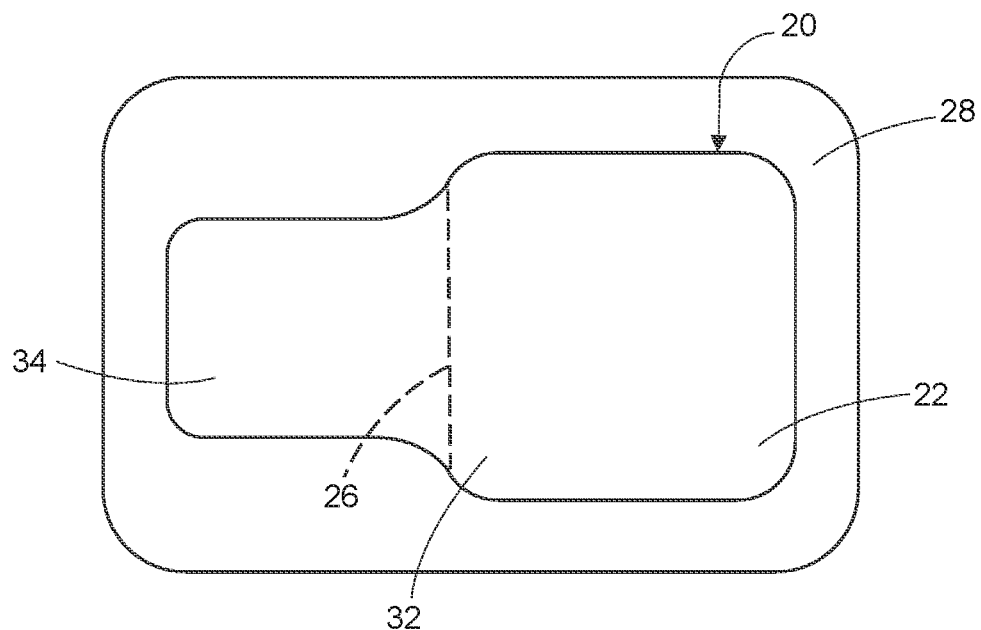
FIG. 3 a top plan view of an exemplary medical electrode including the conductive composition of the present disclosure.
Figure 4:
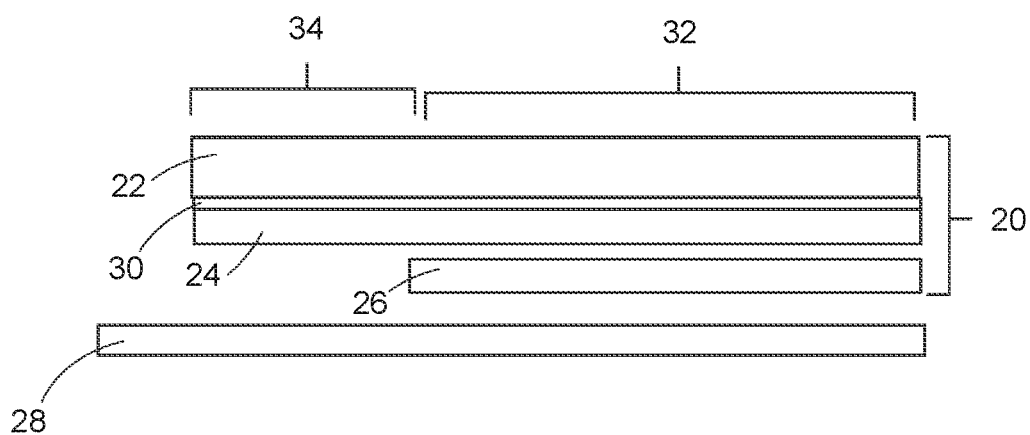
FIG. 4 is a cross-sectional view of the medical electrode of FIG. 3.

Referring to FIGS. 3 and 4, a medical electrode 20 with a release liner 28 is illustrated. The electrode 20 may be a disposable ECG electrode, for example. Electrode 20 includes a backing layer 22, conductive layer 30 adjacent backing layer 22, a conductive ink layer 24 applied to conductive layer 30, and conductive adhesive layer 26 for contacting a patient's skin after removal of the release liner 28.

The electrode 20 includes a conductive interface portion 32 and a tab portion 34 extending beyond the conductive adhesive layer 26 for electrical contact with electrical instrumentation (not shown) by a lead wire or clip.

The backing layer 22 of the medical electrode 20 may be constructed from a layer of generally flexible material such as polyethylene, polyvinyl polyester or a mylar film. These materials allow the backing layer 22 to be light-weight, flexible and resilient. Those skilled in the art will appreciate the extensive list of materials which may be used to form the backing layer 22.

The backing layer 22 may be solid and vapor impermeable, or perforated and vapor permeable, as desired, in view of the intended application. The backing layer 22 may be stamped or cut from either sheet stock or ribbon stock. In one embodiment, the backing layer 22 includes polyethylene film having a thickness in the range of about 0.25 to 5 mil, or in another example, in the range of about 0.5 mil to 4 mil, or in another example, in the range of about 1 mil to 3 mil.

The conductive layer 30 may be a conductive film or coating, such as a film of graphite vinyl, or a graphite containing ink layer, for example.

The conductive ink layer 24 adjacent to the bottom surface of the conductive layer 30 may be the silver/silver chloride ink discussed above.

The medical electrode 20 is placed on the skin of a patient (not shown) to be the metal-electrolyte interface where current in the body (flow or ions) becomes a flow of electrons so that medical equipment can recognize the signal. This transduction is achieved by the movement of Cl atoms on to and off of the Ag atoms. When a $Cl^-$ ion binds to the Ag metal, it donates an electron to the metal and when it debinds it takes an electron with it.

The silver coated inert particles included in the ink layer 24 must have a sufficient amount of silver in the silver coating to maintain this redox reaction throughout the shelf life of the medical electrode. Generally, a medical electrode has a shelf-life of at least two years. The plated particles of the present invention have a greater amount of silver than conventional silver coated inert particles, which enables the medical electrode to meet the two year shelf-life.

In the medical electrode 20, the conductive ink layer 24 may have a thickness in the range of about 0.05 to 5 mil, or in another example, in the range of about 0.1 to 3 mil, or in another example, in the range of 0.1 mil to 0.5 mil.

Printing of the ink layer may be carried out using conventional printing processes such as flexography, gravure and screen printing. These processes allow for the production of very thin continuous uniform coatings with multiple prints at high throughput and low manufacturing cost. With flexography, the content that needs to be printed is on a relief of a printing plate, which may be made from rubber. This plate is inked and that inked image is subsequently transferred to the printing surface. With gravure, an image is engraved into a printing cylinder. That cylinder is inked and the ink is subsequently transferred to the printing surface. Screen printing relies on a woven piece of fabric. Certain areas of this mesh are coated with a non-permeable material. In the remaining open spaces, ink can be pushed through the mesh onto a substrate. The advantages of screen printing are that the surface of the recipient does not have to be flat, it does not require large print runs and can be used for intricate printing patterns.

To achieve consistent coating quality, the coating parameters, such as coating thickness, web speed, oven temperature and air flow rate are optimized. If dilution of the ink is needed, the coating parameters should be adjusted accordingly to match changes in ink properties, such as percentage of solids, viscosity and solvent drying rate.

The conductive adhesive layer 26 may be applied to the bottom surface of the ink layer 24 opposite the backing layer 22, as shown in FIG. 3. The conductive adhesive layer 26 provides for electrical coupling to the body of a patient (not shown). The adhesive layer 26 may be either a conductive adhering or "sticky" gel or a conductive pressure-sensitive adhesive. Preferably, the conductive adhesive layer 26 a conductive gel capable of adhering to the skin. A variety of conductive adhesives known to those skilled in the art may be utilized to provide both sufficient electrical interface between the subject and the electrical instrumentation and sufficient adhesion during the period of evaluation. For example, the adhesive layer 26 may be made of a hydrogel composed of cross-linked polymers such as UV curable polyethylene oxide, polyAMPS or polyvinylpyrrolidone or made from a salt solution. Sodium chloride is commonly used because it is very stable, there are a high concentration of ions (conductive) and it is very compatible with the abundance of sodium and chloride ions in the body. In one example, the adhesive layer 28 has a thickness in the range of 1 mil to 5 mil, or in another example, 2 mil to 4 mil.

Release liner 28 may be attached to the bottom of adhesive layer 26 opposite the ink layer 24 in order to preserve the adhesive character of the gel layer until ready for use. The release liner 28 may be made of a waxed or coated plastic, such as a silicone coated polyethylene terephthalate film.

Figure 5:
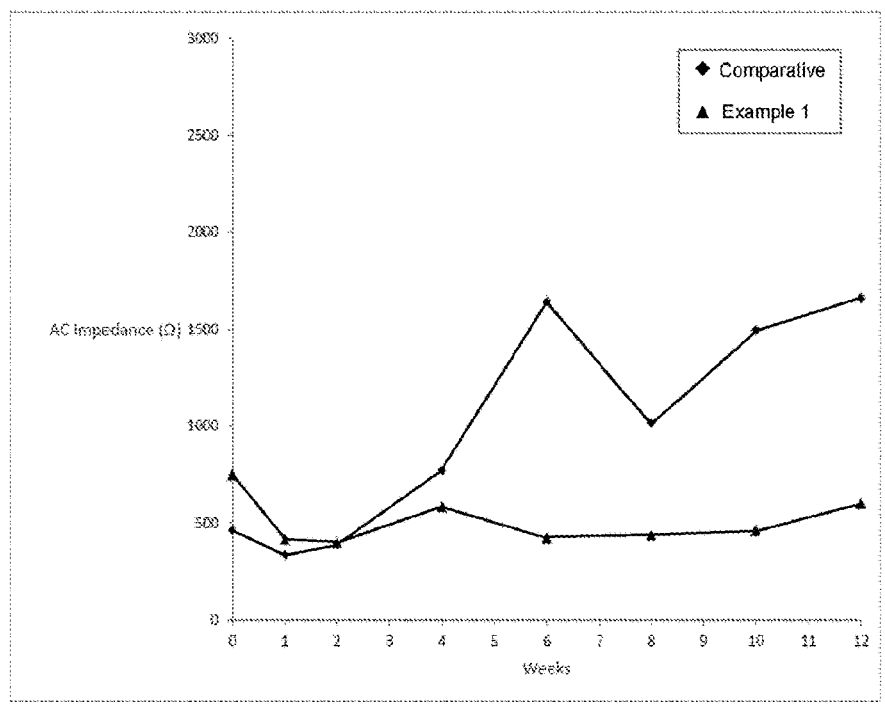
FIG. 5 is a graph showing the results of accelerated aging testing of an electrode made in accordance with the present invention as compared to one made using a commercially available Ag coated particle.

Referring to FIG. 5, which shows the results of accelerated aging testing of an electrode made in accordance with the present invention as compared to one made using a commercially available Ag coated particle. An electrode was constructed using a Ag/AgCl ink containing Ag coated glass particles as described herein, the Ag content of the coated glass particles was 55 wt % based on the weight of the coated glass particles. A second comparative electrode was constructed in the same manner, but using commercially available glass flakes coated with 55 wt % silver based on the weight of the coated flakes. Both ink formulations contained a total of 25 wt % silver, all of the silver content being contributed by the silver on the inert particles. As can be seen from the graph, the electrode constructed in accordance with the present description (Example 1) exhibited unexpectedly better stability and lower impedance throughout the 12-week testing (ANSI/AAMI EC12:2000/(R)2010).

While the medical electrode has been described above in connection with a disposable biomedical electrode for ECG applications, it will be appreciated that it may be used as an electrode for electroencephalographs (EEG) applications, electromyographs (EMG) applications, as defibrillation electrodes or transcutaneous electrical nerve stimulation (TENS) electrodes.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A conductive composition comprising based on dry weight:
    5-30% silver coated glass flakes having a particle size in the range of 5 μm to 75 μm, and having a silver content in the range of 15 wt % to 49 wt %, based on the weight of the coated glass flakes;
    5-30% AgCl; and
    5-30% polymeric binder;
    wherein the surface area ratio of Ag/AgCl is in the range of 1:2 to 8:1.

2. The conductive composition of claim 1, further comprising 0.5-25 wt % Ag particles.

3. The conductive composition of claim 2, wherein the Ag particles comprise Ag flakes and the Ag flake content is within the range of 5-20% by weight.

4. The conductive composition of claim 3 wherein the Ag flake particles have an average particle size of 5 microns to 45 microns.

5. The conductive composition of claim 1, wherein the AgCl has an average particle size in the range of 0.1 micron to 15 microns.

6. The conductive composition of claim 1, wherein the particles and binder are dispersed in 10-90 wt % organic solvent.

7. The conductive composition of claim 1, wherein the silver coated glass flakes comprise 15 wt % to 45 wt % silver based on the weight of the coated glass flakes.

8. The conductive composition of claim 7, wherein the average particle size of the silver coated glass flakes is within the range of 5 microns to 20 microns and the coated glass flakes comprise 35 wt % to 45 wt % silver and 55-65 wt % glass.

9. The conductive composition of claim 7, wherein the average particle size of the silver coated glass flakes is within the range of 10 to 75 microns and the coated glass flakes comprise 15 wt % to 35 wt % silver and 65-85 wt % inert glass.

10. The conductive composition of claim 1, wherein the specific surface area of the silver coated glass flakes in within the range of 0.3 to 1.2 $m^2/g$.

11. A biomedical electrode comprising:
   a conductor comprising an electrically conductive surface;
   a conductive ink layer in electrical contact with the conductor, the ink layer comprising the conductive composition of claim 1;
   an electrically conductive adhesive in electrical contact with the conductive ink layer.

12. The biomedical electrode of claim 11, wherein the electrically conductive surface comprises a graphite loaded polymer.

13. The biomedical electrode of claim 11, further comprising a non-conductive backing layer having a first side comprising a first major surface and a second side comprising a second major surface, the electrically conductive surface associated with the second major surface of the non-conductive backing and the electrically conductive adhesive associated with the electrically conductive surface.

14. The biomedical electrode of claim 11, wherein the electrically conductive adhesive comprises a pressure sensitive adhesive.

15. The biomedical electrode of claim 11, wherein the electrically conductive adhesive comprises a hydrogel.

16. The biomedical electrode of claim 11, wherein the non-conductive backing further comprises a tab portion and a conductive interface portion, the first major surface and the second major surface shared by the tab portion and the conductive interface portion, at least a portion of the electrically conductive adhesive being disposed over the second major surface on the conductive interface portion, the electrically conductive adhesive associated with the electrically conductive surface on the conductive interface portion.

17. The biomedical electrode of claim 11, further comprising a release liner disposed over the electrically conductive adhesive.

18. The biomedical electrode of claim 11, wherein the inert particles of the conductive composition comprise glass.

19. The biomedical electrode of claim 11, wherein the conductive composition further comprises Ag flakes and the Ag flake content is within the range of 0.5-25% by weight of the ink layer.

20. The biomedical electrode of claim 11, wherein the silver coated glass flakes of the conductive composition comprise 15 wt % to 45 wt % silver based on the total weight of the coated glass flakes.

\* \* \* \* \*